United States Patent [19]

Knoch et al.

[11] Patent Number: 4,995,881
[45] Date of Patent: Feb. 26, 1991

[54] HEART VALVE PROSTHESIS

[75] Inventors: Martin Knoch; Helmut Reul; Günter Rau, all of Aachen, Fed. Rep. of Germany

[73] Assignee: B. Braun Melsungen AG, Melsungen, Fed. Rep. of Germany

[21] Appl. No.: 387,701

[22] Filed: Jul. 31, 1989

[30] Foreign Application Priority Data

Aug. 25, 1988 [DE] Fed. Rep. of Germany ....... 3828830

[51] Int. Cl.⁵ .............................................. A61F 2/24
[52] U.S. Cl. ....................................................... 623/2
[58] Field of Search ............................................ 623/2

[56] References Cited

U.S. PATENT DOCUMENTS 4,326,304 4/1982 Klawitter .
4,799,930 1/1989 Knoch et al. ................................. 623/2

FOREIGN PATENT DOCUMENTS 1163054 3/1984 Canada .................................... 623/2
3028981 2/1981 Fed. Rep. of Germany .

Primary Examiner—David J. Isabella
Assistant Examiner—Stephanie L. Iantorno
Attorney, Agent, or Firm—Spensley, Horn, Jubas & Lubitz

[57] ABSTRACT

A heart valve prosthesis, the inner surface of the valve ring of which continuously narrows in flow direction, is provided with a special manner of supporting the closing members. The valve ring is provided with sector-shaped recesses into which a respective oblong journal pin of the closing member extends. In the opening and closing movement, the journal pin sweeps the bottom of the recess like a windshield wiper. Thus, a formation of thrombi in the vicinity of the bearings is prevented.

18 Claims, 2 Drawing Sheets

HEART VALVE PROSTHESIS

BACKGROUND OF THE INVENTION

1. Field of the Invention

The invention relates to a heart valve prosthesis.

2. Description of Related Art

A heart valve prosthesis of this type is known from German Pat. No. 37 01 755 C1. The known heart valve prosthesis is provided with a valve ring, the inner surface of which constantly narrows along its entire length in the flow direction. At least one closing member is pivotably supported in this valve ring. The closing member consists of a pivotal flap provided with journal pins along the rotational axis that are supported in recesses in the inner wall of the valve ring.

There is a danger with heart valve prostheses that thrombi may be formed in dead water areas occurring in the region of the journal pins of the closing members. For this reason, case has to be taken that no blood corpuscles can settle in the recesses or at the journal pins. Another problem occurring with heart valve prostheses in which the diameter of the valve ring varies in the flow direction, is that the closing members on the one hand, should tightly close the opening of the valve ring in the closed position, but should also be pivoted to the open position without jamming. Heart valve prostheses are known in which the rotational movement of the closing member is simultaneously superimposed by a translational movement. Such a combination of rotational movement and translational movement is not possible with valve rings having a diameter which varies in the flow direction, because this would impair either the nonjamming property or the tightness. However, if the journal pins and the corresponding recesses are of cylindrical shape, corpuscles will settle in the annular space existing therebetween, which gives rise to the forming of thrombi.

It is an object of the invention to provide a heart valve prosthesis that allows a non-jamming movement of the closing body, while providing a tight sealing in the closed position, and in which the journal pins execute movements in the recesses whereby the blood in the recesses is wiped out upon every movement of the closing member.

SUMMARY OF THE INVENTION

In the heart valve prosthesis of the present invention, the journal pins have an oblong shape. Their opposite ends are provided with supporting surfaces, the first surface being effective in the closed position to firmly press the closing member against the inner surface of the valve ring, and the second supporting surface supporting the closing member in the open position against the pressure of the flowing blood. Each oblong journal pin is accommodated in a sector-shaped recess in which it moves like a windshield wiper during the opening and closing movements, in order to wipe out the blood contained in the recess. Thus, a well defined rotational axis is maintained for each closing member, the position of which axis does not change during the opening and closing movements, and, simultaneously, a supporting of the journal pin is provided at both ends in every position of slewing. The oblong journal pin executes pivoting movements within the recess. In the closed position, the edge of the closing member is pressed against the inner surface of the valve ring diverging in upstream direction with respect to the flow direction, without any jammings occurring during the opening.

If a closing member is supported in a valve ring having a cross-sectional surface which decreases in the flow direction, the peripheral edge of the closing member will interfere in the opening position with the inner surface of the ring. This requires that a recess be provided at the ring or the closing member. Such recesses should be made as small as possible in order to achieve laminar flow conditions. This is achieved by providing that the tangent lines at the inner surface of the valve ring and at the peripheral edge of the closing member coincide in the rotational axis.

The radius of the second supporting surface which engages the peripheral region of the sector-shaped recess is considerably larger than the radius of the first supporting surface which engages the rounded inner region of said recess. On the other hand, the second supporting surface may be provided with a smaller size than the first supporting surface, since the second supporting surface, being effective in the open position of the closing member, is exposed to lesser supporting forces. A suitable dimensioning of both supporting surfaces allows the local surface pressures on the support surfaces to be kept low, resulting in a long durability of the heart valve prosthesis.

It is a further advantage of the sector-shaped recess for receiving the journal pin that this recess can receive one of the overlapping areas in which, if there were no recess, the edge of the closing member would collide with the inner surface of the valve ring.

BRIEF DESCRIPTION OF THE DRAWINGS

The following is a detailed description of an embodiment of the present invention with reference to the accompanying drawings.

In the Figures

DESCRIPTION OF THE PREFERRED EMBODIMENTS

Figure 1:
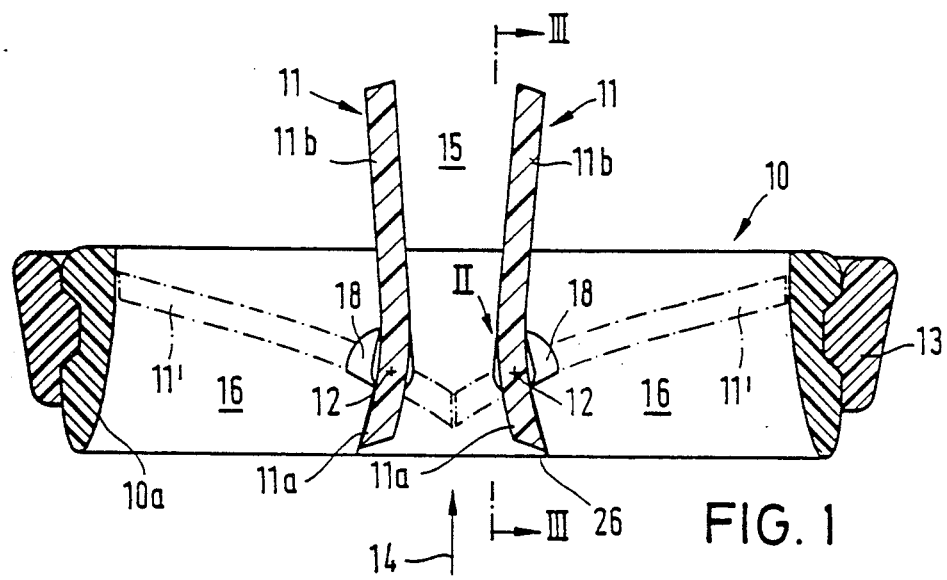
FIG. 1 is a longitudinal section of a preferred embodiment of the heart valve prosthesis of the present invention.

The embodiment described below is a bileaflet heart valve prosthesis having a circular valve ring 10 in which two closing members 11 in the form of bent plates are respectively pivotably around a swivel axis 12. The outer surface of the valve ring 10 is provided with a circumferential groove having a suture ring 13 seated therein for allowing the suturing of the heart valve prosthesis to the tissue. The flow direction during the systole is indicated by the arrow 14.

The inner surface 10a of the valve ring 10 constantly decreases in the flow direction from the inlet to the outlet. Each of the closing members 11 is of an approximately semi-circular shape and forms—with respect to the swivel axis 12—a double-art lever. In the closed position, the shorter portions 11a of the closing members abut the central plane of the ring 10 with their edges whereas the longer portions 11b sealingly abut against the inner surface 10a with their circumferential edges. The closed position of the closing members 11 is represented by broken lines in FIG. 1. In the open position, the closing members 11 define a nozzle-shaped passage 15 and each closing member together with the inner surface 10a defines an approximately semi-circular passage 16. The closing members 11 are brought into the closed position by the blood pressure during the diastole, whereas they are opened in the direction of arrow 14 by the systolic pressure.

Each closing member 11 is provided along the respective swivel axis 12 with two journal pins 17 projecting in opposite directions, each of the journal pins extending into a recess 18 of the valve ring 10.

Figure 2:
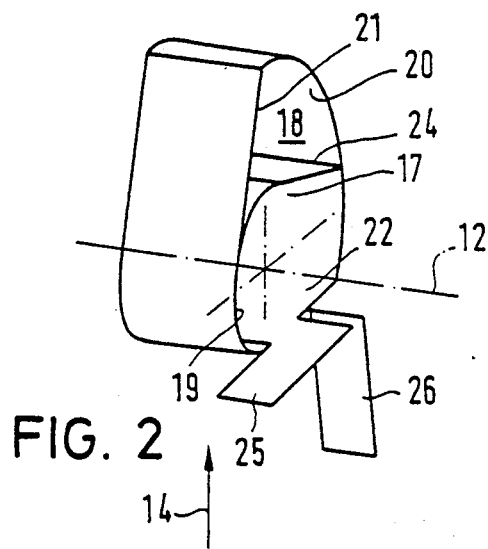
FIG. 2 is a schematic illustration of a bearing, as viewed from the direction of arrow II in FIG. 1.
Figure 3:
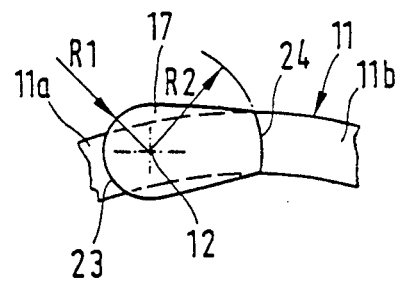
FIG. 3 is a front view of one of the closing members with a journal pin.

As is apparent from FIGS. 2 and 3, the recess 18 is provided in the shape of a sector, the inner portion 19, forming the sector angle, being rounded in a circular arc shape. The peripheral or outer portion 20 of the sector forms a concave surface which faces the concave surface of the region 19. The radial wall 21 of the recess 18 extends substantially parallel to the flow direction (arrow 14), whereas the other wall 22 extends essentially in the direction taken by the closing member in the closed position 11'. The angle between the radial walls 21 and 22 is about 70°. It approximates the swivel angle of the closing member 11.

Journal 17 is situated in the recess 18 and comprises a semi-cylindrical first supporting surface 23 and a circular arc-shaped second supporting surface 24. The first supporting surface 23 curves around the swivel axis 12 with the radius R1 and the second supporting surface 24 curves around the swivel axis 12 with the radius R2. Swivel axis 12 lies between the supporting surfaces 23 and 24. Radius R2 is about twice the radius R1. Journal 17 is of oblong cross-sectional shape, supporting surface 23 pointing towards portion 11a and supporting surface 24 pointing to portion 11b of the closing member.

Journal 17, seated in the recess 18, is supported at the inner portion 19 by the supporting surface 23, whereas the supporting surface 24 contacts the outer portion 20. Journal 17 is pivotable around the swivel axis 12, contacting the radial wall 21 when in the open position and contacting the radial wall 22 of the recess 18 when in the closed position according to FIG. 2. During the swivel movement, the supporting surface 23 rolls off the inner portion 19, whereas the supporting surface 24 moves along the outer portion 20. Since the journal pin 17 does not fill the recess 18, the journal pin executes a displacement during every swivel movement, whereby the blood in the recess 18 is displaced and the recess is flushed.

Figure 4:
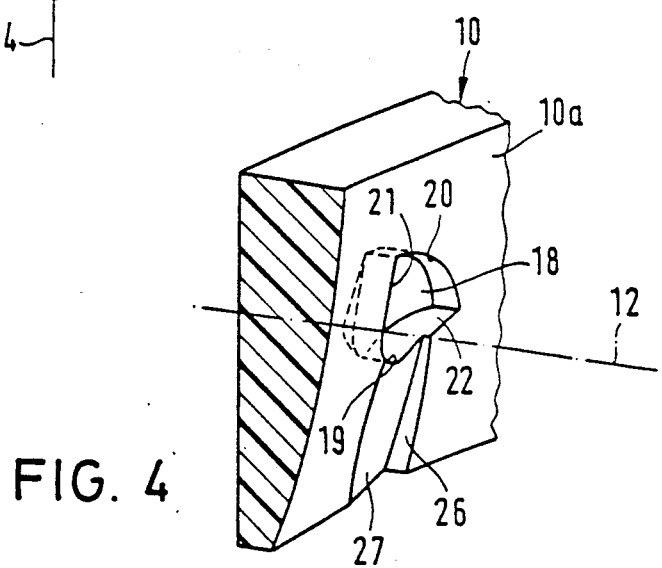
FIG. 4 is a section of the valve ring along line III—III in FIG. 1.

FIG. 2 diagrammatically shows an abutment surface 25 in connection with the journal pin 17 which cooperates with an abutment surface 26 of the valve ring 10 and which limits the opening movement of the closing member. Another view of the abutment surface 26 is shown in FIG. 4. This abutment surface defines the end of a recess 27 extending upstream within the inner surface 10a from the recess and which serves, on the one hand, to prevent collisions of the edge of the closing member with the valve ring in the opening movement and to receive the edge of the closing member in the closed position, and which, on the other hand, allows a simple realisation of abutment surface 26. It is a further purpose of the recess 27 to facilitate the mounting of the closing member in the valve ring.

Figure 5:
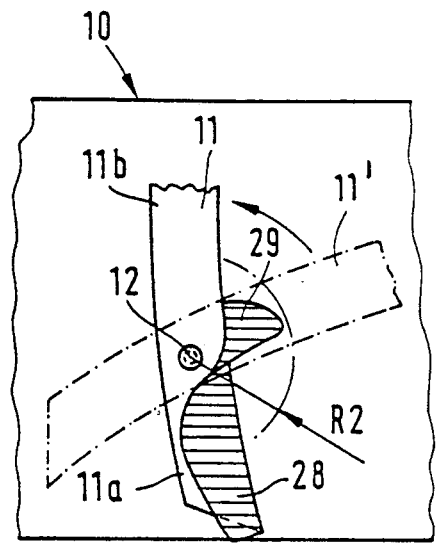
FIG. 5 illustrates the overlapping areas in which the closing member and the valve ring would collide, if no corresponding recesses were provided.

The full lines in FIG. 5 indicate the position of the closing member 11 within the valve ring 10 in the open position, whereas the dotted lines indicate the position of the closing member 11 within the valve ring 10 in the closed position. The hatched portions 28 and 29 indicate the areas of interference, in which, if no additional measures are taken, the edge of the closing member would overlap with the inner surface 10a of the valve ring, maintaining a certain radial clearance that must not be exceeded for reasons of tightness. The measure taken to avoid the interference surface 29 in the closed position of the closing member consists of providing the radius R2 of the supporting surface 24 or the radius of the outer portion 20, relative to the swivel axis 12, with at least the size of the interference area. In other words: if the journal pin 17 were not present, the peripheral edge of the closing member 11 would drop slightly into the recess 18 in the closed position.

Figure 6:
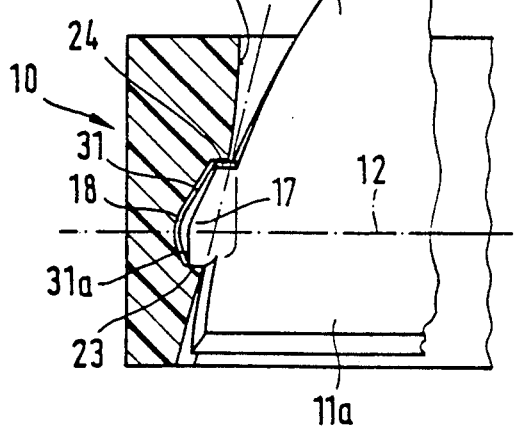

As is apparent from FIG. 6, the tangent line 30a to the inner surface 10a of the valve ring at the swivel axis 12 and the tangent line 30b to the peripheral edge of the closing member 11 at the swivel axis 12 coincide at the swivel axis 12 in the open position. Thus, the sizes of the interference areas 28 and 29 as of FIG. 5 are minimized.

Since the inner side of the valve ring diverges in the upstream direction, the inner portion 19 and the outer portion 20 of the sector-shaped recess 18 are mutually offset in the direction of the swivel axis 12 accordingly, the supporting surface 24 is closer to the longitudinal axis of the ring than the supporting surface 23. In the region adjacent to supporting surface 24, the end surface 31 of the journal pin conically extends obliquely outward. The portion 31a of the end surface of the journal pin, situated in the vicinity of the swivel axis 12, is of spheric shape and tangentially merges into the conical portion. The entire end surface 31 corresponds to a section of an area of rotation around the swivel axis 12, since the wiping movement of the journal pin 17 is restricted to rotation only.

As is further apparent from FIG. 6, the extension of the end surface 31 of the journal pin is adapted to the extension of the bottom of recess 18 such that both extend parallel to each other, maintaining a certain clearance. Thus, the journal pin 17 completely sweeps over and washes out the recess 18 in one swivel movement of the closing member 11.

Figure 7:
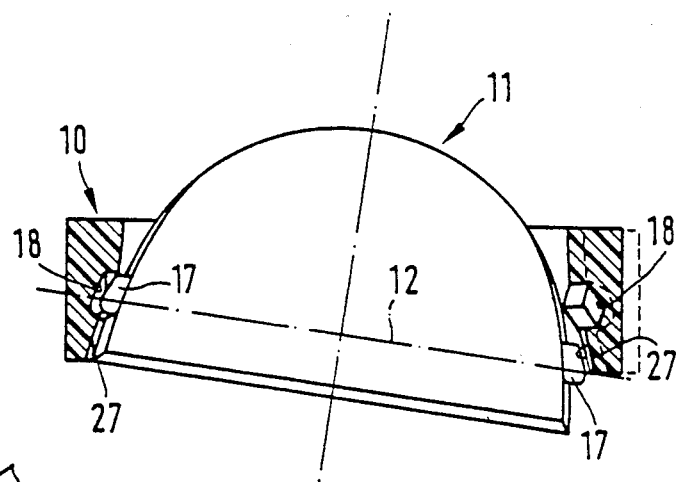
FIG. 6 is a longitudinal section of the bearing with the closing member in the open position and FIG. 7 illustrates the mounting of the closing member in the valve ring.

FIG. 7 shows the insertion of the closing member 11 into the valve ring 10. FIrst, one journal pin 17 is inserted into the corresponding recess 18 and the other journal pin 17 is then pushed into the corresponding recess 18 from the upstream end, sliding in recess 27 with the conical portion of the end face 31 of the journal pin. This causes a short widening of the valve ring, as indicated by the dotted lines in FIG. 7.

What is claimed is:

1. A heart valve prosthesis comprising a valve ring the inner surface of which constantly narrows in flow direction, and at least one closing member provided with journal pins for pivotally engaging in recesses about a swivel axis arranged in the constricted portion of said valve ring, characterised in that each of said recesses is provided in the shape of a sector with a rounded inner portion and an outer portion and that said journal pins are oblong in cross-section and engage at the inner portion of the sector with a first supporting surface and at the outer portion of said sector with a second supporting surface, the swivel axis coinciding with the axis of the curvature of the first supporting surface.

2. The heart valve prosthesis according to claim 1, wherein the closing member is movable between an open position and a closed position, characterised in that a tangent line to the inner surface of said valve ring at said swivel axis and a tangent line at the peripheral edge of said closing member at said swivel axis are substantially coincident when the closing member is in the open position.

3. The heart valve prosthesis according to claim 1, characterised in that the radius of said second supporting surface—relative to said swivel axis—is substantially larger than that of said first supporting surface whereas the peripheral extension of said second surface is smaller than that of the first supporting surface.

4. The heart valve prosthesis according to claim 1, wherein the constantly narrowing inner surface of the valve ring diverges in an upstream direction and converges in a downstream direction and defines a longitudinal ring axis, the first supporting surface is directed substantially in the upstream direction, the second supporting surface is directed substantially in the downstream direction, and wherein the second supporting surface is closer to the ring axis than the first supporting surface.

5. The heart valve prosthesis according to claim 1, wherein said journal pins have end surfaces comprising a first portion and a second portion substantially adjacent to said second supporting surface, characterised in that the second portions of the end surfaces of the journal pins converge toward the second supporting surface in a direction parallel to said swivel axis.

6. The heart valve prosthesis according to claim 1, characterised in that the end surface of said journal pin sweeps the entire bottom of said recess.

7. The heart valve prosthesis according to claim 1, wherein said recess has a bottom and characterised in that the bottom of said recess defines a surface of rotation around said swivel axis.

8. The heart valve prosthesis according to claim 1, wherein said recess has a bottom and characterised in that the bottom of said recess is shaped spherically in the vicinity of said swivel axis and conically downstream of said swivel axis.

9. The heart valve prosthesis according to claim 1, wherein said closing member has an edge substantially adjacent the journal pin and characterised in that upstream of said recess a second recess is provided in said valve ring for receiving the edge of said closing member in the closed position, said second recess having an abutment for limiting the open position.

10. A heart valve prosthesis comprising:
a valve ring having a continuously narrowing inner surface, the inner surface having a plurality of recesses,
a closing member having a swivel axis and being provided with a plurality of journal pins, at least one of the plurality of journal pins being configured to engage at least one of the plurality of recesses,
at least one of the plurality of recesses being sector-shaped and having a rounded inner portion and an outer portion,
at least one of the journal pins defining a substantially oblong cross-section and having a first supporting surface configured to engage the rounded inner portion of the recess and a second supporting surface configured to engage the outer portion of the recess,
the first supporting surface defining an axis of curvature,
the swivel axis and the axis of curvature of the first supporting surface being substantially coincident.

11. The heart valve prosthesis according to claim 10, wherein the closing member defines a peripheral edge, the inner surface of the valve ring adjacent the swivel axis defines a first tangent line, the peripheral edge of the closing member adjacent the swivel axis defines a second tangent line, and wherein the first tangent line and the second tangent line are substantially coincident.

12. The heart valve prosthesis according to claim 10, wherein the first supporting surface defines a first radius and a first peripheral extension, the second supporting surface defines a second radius and a second peripheral extension, and wherein the second radius is larger than the first radius and the second peripheral extension is smaller than the first peripheral extension.

13. The heart valve prosthesis according to claim 10, wherein the continuously narrowing inner surface of the valve ring diverges in an upstream direction and converges in a downstream direction and defines a longitudinal ring axis, the first supporting surface is directed substantially in the upstream direction, the second supporting surface is directed substantially in the downstream direction, and wherein the second supporting surface is closer to the ring axis than the first supporting surface.

14. The heart valve prosthesis according to claim 10, wherein at least one of the journal pins has an end surface, the end surface comprising a first portion and a second portion substantially adjacent to the second supporting surface, the second portion of the end surface converging toward the second supporting surface in a direction parallel to the swivel axis.

15. The heart valve prosthesis according to claim 10, wherein at least one of the journal pins has an end surface, at least one of the recesses has a bottom, and wherein the end surface of the journal pin is configured to sweep the entire bottom of the recess.

16. The heart valve prosthesis according to claim 10, wherein at least one of the recesses has a bottom, and wherein the bottom of the recess defines a surface of rotation around the swivel axis.

17. The heart valve prosthesis according to claim 10, wherein the continuously narrowing inner surface of the valve ring diverges in an upstream direction and converges in a downstream direction, wherein at least one of the recesses has a bottom, and wherein the bottom of the recess is spherically shaped in the vicinity of the swivel axis and conically shaped downstream of the swivel axis.

18. The heart valve prosthesis according to claim 10, wherein the continuously narrowing inner surface of the valve ring diverges in an upstream direction and converges in a downstream direction, wherein the closing member has an edge and is moveable about the swivel axis between an open position and a closed position, and wherein an additional recess is provided in the valve ring upstream of at least one of the plurality of recesses, the additional recess being configured to receive the edge of the closing member in the closed position, the additional recess having an abutment for limiting the closing member in the open position.

* * * * *